United States Patent [19]

Tanke et al.

[11] Patent Number: 5,043,265
[45] Date of Patent: Aug. 27, 1991

[54] INORGANIC PHOSPHOR LABELLED MACROMOLECULES; A PROCESS FOR THEIR PREPARATION AND THEIR USE FOR IMMUNOLOGICAL OR IMMUNOCYTOCHEMICAL ASSAYS

[75] Inventors: Hendrikus J. Tanke, Rijnsburg; Johannes C. Slats, Noordwijkerhout; Johan S. Ploem, Oegstgeest, all of Netherlands

[73] Assignee: 501 Rijksuniversiteit leiden, Netherlands

[21] Appl. No.: 45,060

[22] PCT Filed: Aug. 4, 1986

[86] PCT No.: PCT/NL86/00022
§ 371 Date: Mar. 26, 1987
§ 102(e) Date: Mar. 26, 1987

[87] PCT Pub. No.: WO87/00926
PCT Pub. Date: Feb. 12, 1987

[30] Foreign Application Priority Data

Aug. 5, 1985 [NL] Netherlands ............... 8502187

[51] Int. Cl.$^5$ ............... G01N 33/533; G01N 33/551
[52] U.S. Cl. ............... 435/6; 427/2; 435/7.92; 435/973; 435/7.2; 435/7.21; 436/501; 436/524; 436/547; 436/800; 436/805; 530/389; 530/391; 536/27

[58] Field of Search ............... 436/172, 524, 544, 547, 436/805, 56, 501, 800; 530/389, 391; 536/27; 427/2; 252/301.36; 435/6, 7

[56] References Cited

U.S. PATENT DOCUMENTS

| Re. 30,015 | 5/1979 | Lipp ............... 313/473 |
| 2,478,387 | 8/1949 | Graham et al. ............... 252/301.36 |
| 3,915,707 | 10/1975 | Gesswein et al. ............... 252/301.36 |
| 4,000,252 | 12/1976 | Kosak ............... 436/535 |
| 4,452,861 | 6/1984 | Okamoto et al. ............... 428/402.24 |

FOREIGN PATENT DOCUMENTS 2095258  9/1982  United Kingdom .

Primary Examiner—David A. Saunders
Attorney, Agent, or Firm—Morgan & Finnegan

[57] ABSTRACT

The invention relates to macromolecules, such as proteins, including immunologically specific antibodies, lipoproteins, polynucleotides, etc., provided with luminescent labels.

The invention further relates to a process for preparing macromolecules, such as proteins, including immunologically specific antibodies, lipoproteins, polynucleotides, etc., provided with luminescent labels, and also to the use of labelled immunologically specific macromolecules, such as antibodies, for immunological or immunocytochemical assays.

14 Claims, No Drawings

INORGANIC PHOSPHOR LABELLED MACROMOLECULES; A PROCESS FOR THEIR PREPARATION AND THEIR USE FOR IMMUNOLOGICAL OR IMMUNOCYTOCHEMICAL ASSAYS

The invention relates to macromolecules, such as proteins, including immunologically specific antibodies, lipoproteins, polynucleotides, etc., provided with luminescent labels.

The invention further relates to a process for preparing macromolecules, such as proteins, including immunologically specific antibodies, lipoproteins, polynucleotides, etc., provided with luminescent labels, and also to the use of labelled immunologically specific macromolecules, such as antibodies, for immunological or immunocytochemical assays.

In biomedical examinations, use is often made of the specific immunological reaction between antigen and (monoclonal) antibody. To render visible and quantify this reaction, the antigen or the antibody is provided with a label. The most common labels are enzymes that can be demonstrated with specific colour reactions, luminescent compounds, and radioactive isotopes. Prominent among luminescent labels are photoluminescent compounds, such as fluorochromes, although the suitability of bioluminescents and chemiluminescents has been demonstrated (Pratt et al., 1978; Simpson et al., 1979; Hastings and Wilson, 1976).

Apparatus for the qualitative and/or quantitative processing of fluorescence signals (photons) has been greatly improved in the last few years. Single-photon-counting detection systems and highly sensitive cameras of the SIT or ISIT type (with image intensifiers), as well as high-energetic excitation sources, such as lasers, are at present available. To increase the amount of fluorescence, new fluorochromes, such as phycobiliproteins, with a high fluorescence efficiency have been developed (Oi et al., 1983). Polystyrene or latex microspheres, which contain thousands of fluorochrome molecules, have also been introduced as cell labels (so-called Covaspheres) (Molday et al., 1975; European Patent Application EP 0002963 (Eastman Kodak Company), 1979). Thanks to these improvements, the extreme sensitivity of fluorescence studies of cells and tissues is at persent determined for the major part by the autofluorescence of the biological object and the optics used (lenses and filters), and by undesirable excitation light from the radiation source. The autofluorescence of a single cell, measured with a microscope fluorimeter or a flow cytometer, is in the order of several thousands of fluorescein equivalents (Jongkind et al., 1979), as a result of which the demonstration of minute amounts of macromolecule in cells and tissues by means of immunofluorescence is not optimally possible. It is especially for the demonstration of minute amounts of macromolecules, therefore that one would often opt for a method using a radioactive label. This method is sensitive, it is true, but in the case of in situ applications (e.g. autoradiography) extremely time-consuming, while in addition the necessary precautionary measures must be taken with regard to working conditions and the processing of the radioactive waste.

In analytical chemistry, the problem of autofluorescence can be largely avoided by using so-called time-resolved fluorescence assays. For this method a luminescent label must be selected with a long after-glow time, such as the lanthanides europium (eu) and terbium (Tb). After a short exciting light pulse, the relatively fast autofluorescence (in the order of nanoseconds or faster) can be separated in time from the slower lanthanide fluorescence (in the order of milliseconds). The DELFIA (Delayed Fluoro Immuno Assay) system, developed by LKB, makes use of this principle. This method has been found to be competitive in sensitivity with radioactive assays (Soini et al., 1983; Hemmila et al., 1984). One disadvantage is, however, that the luminescent label Eu or Tb when bonded to antibodies and dissolved in water does not luminesce, or hardly so, and therefore after the reaction with the antigen-antibody must be liberated to obtain the delayed-fluorescence properties. As a consequence, detection is only possible in solutions, and uses of this method in which localisation of the antigen at the tissue, cell or chromosomal level is required are impossible. The very low quantum efficiency of the lanthanides in aqueous solutions can be improved considerably by incorporating lanthanides such as e.g. Europium and Terbium by means of cross-linking agents into latex particles, thereby increasing its fluorescence yield (EP 0002963; Eastman Kodak Company, 1979). Thus prepared latex particles can be coupled to cells. It is these very cellular uses which command increasing interest, thanks to the development of molecular biology and the possibility of demonstrating oncogene and virus products in tissues and cells using specific monoclonal antibodies. The present inventors have developed a new immunological label which combines many of the advantages of the existing methods, and in addition permits localisation of the antigen-antibody complex at cell level.

The invention is characterized in that the labels are inorganic crystalline phosphors.

For use in biological systems, the size of the crystalline phosphors must generally not exceed 5 um. Preferably the labels used are crystalline phosphors with a particle size of 1 um or smaller.

Because, on the other hand, the luminescence intensity decreases rapidly with decreasing size of the phosphors, the phosphors should generally have a size of 0.02 um or larger. Preferably, the labels used are crystalline phosphors with a particle size of 0.1 um or larger.

The invention accordingly provides a material comprising a label which is a crystalline phosphor, to which the macromolecule, such as antibody, is adsorbed or chemically bonded. These phosphor labels luminesce blue, green or red (depending on the phosphor used) under a fluorescence microscope (UV excitation) or exhibit cathode luminescence in a scanning electron microscope. As their after-glow time is in the order of msec or sec, phosphor-labelled cells can be measured in accordance with the time-resolved principle with microscope-cyto fluorimeters and flow cytometers adapted for the purpose. With regard to the nature of the inorganic crystalline phosphors, there are no limitations. All known inorganic crystalline phosphors, such as those described in Kirk-Othmer Encyclopedia of Chemical Technology, third edition, Volume 14, pp. 527 ff., and in many patent publications, and also as yet unknown inorganic crystalline phosphors are suitable for use as labels in accordance with the present invention, with their particle size being preferably reduced to 1 um or less.

The use of a stable suspension of inorganic crystalline phosphors with macromolecules (antibodies) physically or chemically attached, has not been described before as (immuno)cytochemical reagent. K. Kosak (U.S. Pat. No. 4,000,252; 1976) has mentioned the use of a phosphor-antibody complex in a new type of immunoscintillation cell for a new radioimmunoassay method. This cell consists of a support medium with organic phosphors incorporated, to which antibodies are coupled. The cell may have different physical shapes. The support medium serves as a trapping agent for the radioactively labelled or unlabelled antigen; binding of a radioactively labelled antigen induces luminescence of the phosphor in its direct vicinity, which is subsequently measured as is done in a scintillation counter. The present patent application does not relate to a solid phase consisting of an organic phosphor-antibody complex, but relates to a stable suspension of an inorganic phosphor-antibody complex, which is used as (immuno)cytochemical reagent. In 1972 L. Amante et al. have studied the properties of conjugates of immunoglobulins with the amorphous and crystalline form of tetramethyl rhodamine isothiocyanate (TRITC). However, the fluorophore TRITC was dissolved from its various native states in water, and subsequently coupled to immunoglobulin.

Before the coupling between the inorganic crystalline phosphors and the macromolecules, such as antibodies, is brought about, the phosphors, which as stated before preferably have particle sizes of 1 um or less, should preferably be subjected to a pre-treatment to provide their surface with charged groups. As a consequence the individual particles will repel each other and the formation of larger aggregates will be avoided. The nature of the charged groups is not critical. Both groups of negative charge, such as carboxylic acid groups, sulphonic acid groups, phosphoric acid groups, and the like, and positively charged groups, such as amino groups and quaternary ammonium groups, are suitable for the effect contemplated.

Experiments conducted and the results achieved therein (see the example) show that, in principle, it is possible to couple antibodies to crystalline phosphors with a particle size of 1 um and smaller in such a manner that specific immunological reactions with this antibody-phosphor conjugate are possible. Of two tested methods, the adsorption of antibodies to phosphors at a pH in the vicinity of the isoelectric point (for IgG 6.6) turned out to be preferred to covalent coupling via suitable spacer molecules. The adsorption method is known per se and, among other applications, is successfully used for coating colloidal gold spheres with antibodies, for use in the electron microscope (Geuze et al., 1981). The use of other coupling methods than the methods herein illustrated, however, is not excluded.

Immunologically positive lymphocytes are easily recognized by means of fluorescence microscopy with UV excitation. A major advantage is that the phosphors used do not exhibit bleaching. Crystals that have not reacted are easily distinguished as small phosphorescent dots in the background. Nevertheless, we prefer to separate the non-reacted phosphor crystals from the cells, for example, by gradient centrifugation, as a result of which a cleaner background is obtained. The relatively small crystals (about 0.2 um) can easily be removed by centrifugation, because these remain behind in the supernatant at (200–400)xg (conventional for cells). Tests in which a density gradient was used also gave good results. The luminescence intensity of phosphor-labelled cells was high. Microscope photography required exposure periods of 1 to 5 sec. Comparable conventional fluorescence colourings of membrane components commonly result in exposure times of 30 to 60 sec., partly owing to the occurrence of bleaching.

The phosphors cannot only be rendered visible to the human eye by means of the fluorescence microscope and the electron microscope. Measurements of the luminescence signal and reproduction thereof by means of a memory oscilloscope show that the time-resolved luminescence measuring principle can be used. This offers the possibility of adapting the apparatus currently available for the quantitative fluorescence analysis of tissues, cells and cell components in such a manner that the specific (slow) phosphorenscence signals can be separated from the interfering (fast) background fluorescence signals and from possibly reflected excitation light. An additional advantage is that the background luminescence of biological objects such as cells virtually exclusively concerns "fast" fluorescence processes.

The apparatus used for the quantitative analysis of cells mainly concerns microscope fluorimeters and flow cytometers. The detection systems of these fluorimeters mostly consist of photomultiplier tubes, photodiodes, television cameras, or arrays of detectors. With a relatively simple electronic circuit, a time delay can be realized between the moment of excitation (in pulsed form) and the moment when the (delayed) luminescence signal is measured. This principle can be used in systems in which the entire microscopic object is bodily excited, but also in systems where the object is scanned point by point by a small excitation light spot (laser scanning, incremental table scanners).

In flow systems in which the excitation of cells flowing past and the measurement of luminescence take place along different optical paths, the time delay can also be realized by positioning the lens registering the luminescence signal somewhat downstream. For example, in a FACS type cell sorter a delay of 100 microseconds can be realized by focussing the detection lens 1 cm lower on the liquid stream.

USES OF PHOSPHOR-LABELLED IMMUNOLOGICAL REAGENTS

In principle, phosphor conjugates are suitable for use in all applications where fluorochrome, enzyme, or isotope-labelled immuno-reagents are used. Examples are ELISA and RIA techniques for demonstrating and assaying antigens in solution, immunological methods for the detection of macromolecules in filter blots, and immunocytochemical methods for the study of morphologically intact tissues and cells. As regards the cytochemical application the accent will be on demonstrating superficial antigens, as phosphor particles of 0.1–1.0 um cannot easily penetrate cell membranes.

By using phosphors, several parameters can be studied and measured at the same time. Not only is it possible to generate three spectrally separate colours (blue, green, red) by means of UV or electron excitation, but phosphors with different decay times can be used, by virtue of which the number of antigens to be measured at the same time can become very large.

Time-resolved luminescence assays are comparable in sensitivity to radioactivity assays (Soini and Kojola, 1983). The immunocytochemical use of phosphor conjugates basically allows a much more sensitive detection of small quantities of macromolecules in cells. This may be of importance in both fundamental and diagnostic examination for membrane-linked oncogene proteins, viral products and differentiation antigens.

In summary, it has accordingly been found that macromolecules, such as immunoglobulins can be adsorbed onto crystalline phosphors with a particle size of 1 um or smaller, and that the resulting conjugates, such as phosphor-antibody conjugates, are immunologically and immunocytochemically specific and applicable. Examples of the properties of the phosphors, other than their high physico-chemical stability are that they can be rendered visible by excitation with UV light or with an electron beam, and that the luminescence of the conjugates, such as phosphor-antibody conjugates, does not decrease during excitation (no bleaching). In addition, the luminescence belongs to the relatively slow luminescence (phosphorescence). As the luminescence decay is in the order of milliseconds, a strong suppression of autofluorescence and undesirable background reflection is possible by means of time-resolved luminescence assays, by virtue of which a high sensitivity can be achieved. The luminescence of phosphors can be observed with microscope fluorimeters and flow cytometers. These can be modified for time-resolved luminescence assays in a relatively simple manner. The use of phosphor-antibody conjugates basically makes it possible to assay a plurality of antigens simultaneously, because the luminescence of phosphors is not only well separated spectrally (blue, green, red), but also exhibits measurable differences in decay times.

The invention is illustrated in and by the following example.

EXAMPLE

(a) Preparation of the phosphors

The starting products were two types of phosphors: a blue one consisting of zinc sulfide (ZnS) activated with silver (Ag), and a red one consisting of yttrium oxysulfide ($Y_2O_2S$) activated with europium (Eu). Both were subjected to a pre-treatment comprising ball-milling the relatively large phosphors (5-6 um) until a crystal size of 1 um or smaller was reached. The phosphors were then treated with polyfunctional polymers, including carboxylic acid, amino, and sulphonic acid groups. The slurry was alkaline stabilized to final pH 9.8-10.0. The ultimate density of the prepared phosphor slurries was 150 g/l. A slight degree of (reversible) aggregation of the crystals was, if necessary, remedied by treating the slurry ultrasonically for 1 minute (energy 40W).

(b) Preparation of the phosphor-antibody conjugates

Two methods were tested

1) The covalent coupling of phosphors containing carboxyl groups among others, to antibodies by means of a spacer of ε-aminocapronic acid introduced with water-soluble carbodiimide (EDC) (Molday et al., 1975; Rembaum, 1979).

This procedure was carried out as follows: The original phosphor slurry was re-suspended in 10 ml 0.01M ε-amino capronic acid (Merck, Darmstadt, Western Germany) and the pH was adjusted to 5.0 with HCl. Density was 25 mg/ml. In 15 minutes, 4×2.5 mg 1-ethyl-3-(3-dimethylaminopropyl) carboiimide (EDC) (Serva, Heidelberg, Western Germany) was added. The reaction period was 2 hours at 4 C. Thereafter the crystals were centrifuged (10 minutes, 1200x g), and washed 3 times with 0.15M NaCl. To 2.0 ml phosphor slurry containing 50 mg solid, 10 mg EDC was added; 1 mg goat anti-mouse total immunoglobulin (Nordic, Tilburg, The Netherlands) was dissolved in 100 ul 0.15M NaCl and slowly added in about 50 minutes. The reaction was carried out at 4 C., with slow stirring for 2 hours. The reaction was then stopped with 0.2 ml 0.1M glycine in $H_2O$, and the crystals were washed 3 times with cold 0.15% NaCl solution (phosphate-buffered) (pH 7.2-7.4).

2) Coupling via strong ionic binding (adsorption).

The original phosphor slurries were diluted in 0.9% NaCl-0.15M HEPES buffer (9:1; pH 7.4) to a density of 0.5 g/l. With careful stirring, goat anti-mouse total immunoglobulins (Nordic, Tilburg, The Netherlands) dissolved in the same buffer were added to 1 ml crystal slurry, final concentrations ranging from 0.25-0.005 mg/ml. Crystal aggregates were re-suspended by an ultrasonic treatment (at 4 C.), for 1 minute, 40W energy.

(c) Immunocytochemical reactions with phosphor-antibody conjugates

The phosphor conjugates prepared by the methods described above were tested for Ficoll-isopaque isolated human mononuclear cells marked with a mouse Leu 3a monoclonal antibody against T helper/inducer cells (Becton Dickinson, Mountain View, Calif.). To 1 ml cell slurry in 0.9% NaCl-0.15M HEPES (9:1; pH 7.4) containing 1 million of cells, 150 ul Leu 3a (1:100) was added. The cells were incubated at room temperature for 30 minutes and washed 3 times with medium. Subsequently, to 1 ml cell suspension, 5-10 ul phosphor-antibody conjugate was added (density 0.5%). The reaction period was 15 minutes at room temperature. The cells were then centrifuged at 150 g for 10 minutes, carefully re-suspended, and washed with medium. There was also prepared a BSA-phosphor conjugate for control purposes.

(d) Fluorescence-microscopy of phosphors and phosphor-antibody-labelled cells The phosphors and phosphor-labelled cells were inspected with a fluorescence microscope (Zeiss, Oberkochen, Western Germany), fitted with a HBO 50W Mercury lamp and a filter set for excitation with UV light (2 mm UG 1-TK 400). An LP 420 filter served as an emission-filter for the blue phosphor crystals and an LP 590 filter for the red phosphor crystals (Schott, Mainz, Western Germany). The objective used was a Zeiss Neofluar 63 X, N.A. 1.25 phase-contrast lens. Total magnification was 630X. The phosphors were also inspected with a scanning electron microscope with a fluorescence-illuminator built-in in the vacuum chamber (Leitz, Wetzlar, Western German) (Ploem and Thaer, 1980). This system makes it possible to view the cathode luminescence of the phosphors generated by the electron beam with the high-aperture fluorescence optics. Emission filters and objective were the same as described above.

(e) Luminescence assays of phosphor crystals by means of microscope photometry and flow cytometry To study the slow luminescence phenomena of the phosphors in the time, the fluorescence microscope was fitted with a 1000W Xenon flash lamp (duration of pulse about 6 microseconds). The luminescence signals were measured with a Zeiss SF microscope-photomultiplier and displayed on a Hewlett Packard 1744A memory oscilloscope. The measuring microscope was interfaced to a PDP 11 microcomputer (Digital Equipment) for automatic control of the Xenon flash lamp and data handling. A program was written for "time-resolved"

luminescence measurements of immunophosphor labelled lymphocytes.

Flow cytometry of phosphor crystal slurries was conducted with a FACS IV cell sorter (Becton Dickinson, Mountain View, Calif.), fitted with an argon ions laser tuned to 100 mW UV (350–360 nm). Luminescence was measured using an LP 420 and an LP 590 emission filter for the flue and red phosphor crystals, respectively. The second flow cytometer used was an ICP 22 (Ortho Diagnostics) with an HBO 100 lamp as the excitation light source and fitted with a filter set for UV excitation. The emission filters were the same as described for the FACS IV experiments.

(f) Results

The two different methods of preparing phosphor-antibody conjugates were compared. The covalent coupling of phosphor crystals to immunoglobulins (method 1) led to strong irreversible aggregation of the crystals that could not be remedied with ultrasonic treatment. Consequently, the yield of unreacted antibody-coupled crystals was very low. As a result the immunocytochemical results of the experiments with Leu-3a-marked lymphocytes were not optimal. Phosphor-marked lymphocytes were observed, it is true, but the major part of the cells turned out to be in large conglomerates of cells and crystals.

Method 2, the adsorption of protein onto phosphor crystals was found not only to be simpler to perform, but additionally led to significantly better results. Specific colouration of the T helper/inducer cell with phosphor-antibody conjugates was observed. The immunological controls used, i.e. mononuclear cells not treated with Leu 3a gave no appreciable reaction with the goat anti-mouse Ig coupled phosphor. Incubations of uncharged phosphor crystals with cells gave no bonding. Furthermore, a BSA phosphor conjugate also prepared for control purposes did not result in significant colouration with mononuclear cells (whether or not marked with Leu 3a).

In all fluorescence microscopy studies, phase-contrast microscopy was used to identify and exclude aspecifically labelled monocytes.

Time-resolved luminescence measurements of immunophosphor labelled cells showed at least a 1 decade improved signal to noise ratio (luminescence contrast) in comparison to conventional cytofluorometry.

The luminescence intensity of the crystals, generated by a Xenon flash lamp was large enough for it to be measured with a Zeiss Photometer microscope and to record the luminescence decay in the time via a memory oscilloscope. The half-life of the luminescence was in the order of magnitude of milliseconds.

It was possible to detect the luminescence of the individual phosphor crystals with flow cytometry (both with laser excitation on the FACS IV, and HBO 100 excitation on the ICP 22).

REFERENCES

1) Pratt J. J., Woldring M. G., Villerius L.: Chemiluminescence-linked immunoassay. J Immunol Meth 21:129:184, 1978

2) Simpson J. S. A., Campbell A. K., Ryall M. E. T., Woodhead J.: A stable chemiluminescent-labelled antibody for immunological assays. Nature 279: 646–647, 1979

3) Hastings J. W., Wilson T.: Bioluminescence and chemiluminescence. Photochem Photobiol 23: 461–473, 1976

4) Oi V. T., Glaser A. N., Stryer L.: Fluorescent phycobiliprotein conjugates for analysis of cells of molecules. J Cell Biol 93: 981, 1982

5) Molday R. S., Dreyer W. J., Rembaum A., Yen S. P. S.: New immunolatex spheres: visual markers of antigens on lymphocytes for scanning electron microscopy. J Cell Biol 64: 75–88, 1975

6) Jongkind J. F., Verkerk A., Visser W. J., van Dongen J. M.: Isolation of autofluorescent "aged" human fibroblasts by flow sorting. Exp Cell Res 138: 409–417, 1982

7) Soini E. and Kojola H.: Time-resolved fluorometer for lanthanide chelates-A new generation of nonisotopic immunoassays. Clin Chem 29: 65: 68, 1983

8) Hemmila, Dakubu S., Mukkala V. M., Siitari H., Lowgren T.: Europium As a label in time resolved immunofluorometric assays Anal Biochem 137: 335–343, 1984

9) Rembaum A.: Microspheres as immunoreagents for cell identification. In: Flow cytometry and sorting. Eds. Melamed M. R., Mullaney P. F., Mendelsohn M. L., p 335–347, 1979

10) Ploem J. S., Thaer J. S.: Luminescence studies with an integrated instrument permitting SEM and fluorescence microscopy of the same specimen. Proc Roy Microsc Soc 15: 9–10, 1980

11) Geuze H. J., Slot J. W., van der Ley P. A., Scheffer R. C. T.: Use of colloidal gold particles in double labelling immunoelectron microscopy of ultrathin frozen tissue section. J Cell Biol 89: 653, 1981

12) Amante L. et al: Conjugation of immunoglobulins with tetramethyl rhodamine isothiocyanate. Comparison between the amorphous and the crystalline fluorochrome. J Immunol Methods 1(3): 289–301, 1972

13) European Patent Application 0002963 Eastman Kodak Company (July 1979): Aqueous stabilized fluorescent labels, proteins labelled therewith and methods of use.

14) U.S. Pat. No. 4,000,252. K. Kosak (December 1976): Immunoscintillation cell.

We claim:

1. An aqueous stabilized suspension of inorganic crystalline phosphor particles having surfaces provided with charged groups and a particle size of 5 um or less, said inorganic crystalline phosphor particles carrying a macromolecular biological substance selected from the group consisting of immunoglobulins, lipoproteins and polynucleotides, said macromolecular biological substance being bound either covalently or by physical adsorption to said inorganic crystalline phosphor particles which can function as a luminescent label of said macromolecular biological substance.

2. An aqueous stabilized suspension as claimed in claim 1 in which the phosphor label has a particle size of 1 um or less.

3. An aqueous stabilized suspension as claimed in claim 1 in which the phosphor has a particle size of 0.02 um to 5 um.

4. A process for preparing an aqueous stabilized suspension of inorganic crystalline phosphor particles having surfaces provided with charged groups and a particle size of 5 um or less said inorganic crystalline phosphor particles carrying a macromolecular biological substance selected from the group consisting of immunoglobulins, lipoproteins and polynucleotides comprising the step of binding said macromolecular biological substance either covalently or by physical adsorption to said inorganic crystalline phosphor particles which can function as a luminescent label of said macromolecular biological substance.

5. A process according to claim 4 in which the phosphor label has a particle size of 1 um or less.

6. A process according to claim 4 in which the phosphor label has a particles size of 0.02 to 5 um.

7. A process as claimed in claim 4 in which the macromolecular substance is bonded to a crystalline phosphor by physical adsorption.

8. A process according to claim 7 in which the bonding is realized at a pH in the vicinity of the isoelectric point of the macromolecular substance.

9. A process as claimed in claim 4 in which the macromolecular substance is covalently bonded to the crystalline phosphors via spacer molecules.

10. A process as claimed in claim 9 in which the bonding is realized via a spacer of E-aminocapronic acid introduced by means of water-soluble carbodiimide.

11. A method for the immunological or immunocytochemical detection of a chemical substance which can be bound specifically by antibodies, said method comprising the steps of (1) contacting a sample possibly containing said substance with an aqueous stabilized suspension of inorganic crystalline phosphor particles having surfaces provided with charged groups and a particle size of 5 um or less, said inorganic crystalline phosphor particles carrying specific antibodies bound either covalently or by physical adsorption to said crystalline phosphor particles which function as a luminescent label of said antibodies, and (2) detecting the luminescent label which is indicative of the presence of said antibodies bound to said substance.

12. The method as claimed in claim 11 wherein the detecting is accomplished by fluorescence microscopy or flow cytometry with UV excitation or by scanning electron microscopy with electron excitation.

13. The method as claimed in claim 11 wherein the detecting is accomplished by time-resolved luminescence assays.

14. A method for the simultaneous detection of at least two different antigens in a biological sample, comprising the steps of (1) treating said sample either simultaneously or consecutively with a first aqueous stabilized suspension of first inorganic crystalline phosphor particles having surfaces provided with charged groups and a particle size of 5 um or less, said inorganic crystalline phosphor particles carrying a first specific antibody capable of binding specifically to one of the antigens to be detected and being bound either covalently or by physical adsorption to said first inorganic crystalline phosphor particles which function as a luminescent label of said first specific antibody and with at least one second aqueous stabilized suspension of second inorganic crystalline phosphor particles having surfaces provided with charged groups and a particle size of 5 um or less, said inorganic crystalline phosphor particles carrying a second specific antibody capable of binding specifically to another of the antigens to be detected and being bound either covalently or by physical adsorption to said second inorganic crystalline phosphor particles which function as a luminescent label of said second specific antibody, and (2) detecting the respective luminescent labels which can be distinguished on the basis of their mutually different spectral characteristics or luminescence decay times and are each indicative of the presence of antibody bound to one of the antigens to be detected.

* * * * *

UNITED STATES PATENT AND TRADEMARK OFFICE
CERTIFICATE OF CORRECTION

PATENT NO. : 5,043,265

DATED : August 27, 1991

INVENTOR(S) : Hendrikus J. Tanke and Johannes C.M. Slats

It is certified that error appears in the above-identified patent and that said Letters Patent is hereby corrected as shown below:

On the title page: Item [75]
Second initial of second named inventor was omitted and should read: Johannes C. M. Slats Address of second named inventor "Noordwikjerhout" should read --Noordwykerhout--.

Title page, item [73], after "Assignee:" delete "501".

Signed and Sealed this

Thirtieth Day of March, 1993

*Attest:*

STEPHEN G. KUNIN

*Attesting Officer*  *Acting Commissioner of Patents and Trademarks*